(12) United States Patent
Gallagher et al.

(10) Patent No.: US 10,709,386 B2
(45) Date of Patent: Jul. 14, 2020

(54) ELECTROCARDIOGRAM WAVEFORM IDENTIFICATION AND DIAGNOSTICS VIA ELECTROPHYSIOLOGICAL SENSOR SYSTEM FUSION

(71) Applicant: LEAR CORPORATION, Southfield, MI (US)

(72) Inventors: David Gallagher, Sterling Heights, MI (US); Francesco Migneco, Saline, MI (US)

(73) Assignee: Lear Corporation, Southfield, MI (US)

(*) Notice: Subject to any disclaimer, the term of this patent is extended or adjusted under 35 U.S.C. 154(b) by 233 days.

(21) Appl. No.: 15/838,539

(22) Filed: Dec. 12, 2017

(65) Prior Publication Data

US 2019/0175114 A1    Jun. 13, 2019

(51) Int. Cl.
| | |
|---|---|
| A61B 5/00 | (2006.01) |
| A61B 5/0452 | (2006.01) |
| A61B 5/0205 | (2006.01) |
| A61B 5/18 | (2006.01) |
| A61B 5/04 | (2006.01) |
| A61B 5/0476 | (2006.01) |
| A61B 5/08 | (2006.01) |

(52) U.S. Cl.
CPC .......... *A61B 5/6893* (2013.01); *A61B 5/0006* (2013.01); *A61B 5/0205* (2013.01); *A61B 5/0452* (2013.01); *A61B 5/18* (2013.01); *A61B 5/04017* (2013.01); *A61B 5/0476* (2013.01); *A61B 5/0816* (2013.01); *A61B 5/7203* (2013.01)

(58) Field of Classification Search
None
See application file for complete search history.

(56) References Cited

U.S. PATENT DOCUMENTS

| | | | |
|---|---|---|---|
| 8,483,909 B2* | 7/2013 | Visconti | B60W 40/09 180/272 |
| 8,847,769 B2* | 9/2014 | Ershov | A61B 5/18 340/575 |
| 9,468,386 B2 | 10/2016 | Braojos Lopez et al. | |
| 9,682,622 B2* | 6/2017 | Kim | H04N 5/23229 |
| 9,688,287 B2 | 6/2017 | Seder et al. | |
| 10,322,675 B2* | 6/2019 | Naboulsi | B60R 1/025 |
| 10,363,846 B2* | 7/2019 | Gallagher | A61B 5/6893 |
| 2003/0146841 A1* | 8/2003 | Koenig | A61B 5/18 340/576 |
| 2006/0068693 A1* | 3/2006 | Kono | A61B 5/14552 454/75 |
| 2013/0070043 A1* | 3/2013 | Geva | B60K 28/066 348/14.02 |

(Continued)

FOREIGN PATENT DOCUMENTS

| | | |
|---|---|---|
| CN | 201414796 Y | 3/2010 |
| WO | 2015086020 A1 | 6/2015 |

*Primary Examiner* — Brian T Gedeon
(74) *Attorney, Agent, or Firm* — Brooks Kushman PC (57) ABSTRACT

An electroencephalography (EEG) sensor is installed on a seat and configured to monitor brain activity of a user to generate a EEG signal. An electrocardiogram (ECG) sensor is installed on the seat and configured to monitor heart activity of the user to generate a ECG signal. A processor of the seat is in communication with the EEG sensor and the ECG sensor, and is configured to process the EEG signal and the ECG signal to determine a stress level of the user.

16 Claims, 8 Drawing Sheets

(56) References Cited

U.S. PATENT DOCUMENTS

| | | | |
|---|---|---|---|
| 2014/0039330 A1* | 2/2014 | Seo .................... | A61B 5/0452 600/509 |
| 2014/0240132 A1* | 8/2014 | Bychkov ................. | A61B 5/18 340/576 |
| 2015/0313475 A1* | 11/2015 | Benson ................ | A61B 5/6893 297/217.3 |
| 2016/0001781 A1* | 1/2016 | Fung .................... | B60W 40/08 701/36 |
| 2016/0135706 A1 | 5/2016 | Sullivan et al. | |
| 2016/0151021 A1 | 6/2016 | Feng et al. | |
| 2017/0172520 A1 | 6/2017 | Kannan et al. | |
| 2017/0340214 A1* | 11/2017 | Benson ............... | A61B 5/6893 |

\* cited by examiner

ELECTROCARDIOGRAM WAVEFORM IDENTIFICATION AND DIAGNOSTICS VIA ELECTROPHYSIOLOGICAL SENSOR SYSTEM FUSION

TECHNICAL FIELD

The present disclosure is generally related to a system for electrocardiogram (ECG) waveform identification and diagnostics via electrophysiological sensor system fusion. In particular, the present disclosure is related to a ECG waveform identification and diagnostics vehicle integration.

BACKGROUND

In modern world, heart conditions and diseases (e.g., cardiac arrest) has become one of the most prevalent issues around the world. Although many of those heart conditions has symptoms that can be detected by doctors, it often requires the patient to go to medical facilities for tests. Alternatively, portable medical equipment has been created. For instance, ECG sensors and processors may be embedded in a piece of clothing (e.g., a vest) worn by the patient to collect heart rate (HR) and ECG data. However, such portable medical equipment requires the patient to wear it regularly, making it inconvenient for everyday use.

SUMMARY

In one or more illustrative embodiments, a vehicle system, comprises an electroencephalography (EEG) sensor installed on a seat configured to monitor brain activity of a user and generate a EEG signal; an ECG sensor installed on the seat configured to monitor heart activity of the user and generate a ECG signal; and a processor in communication with the EEG sensor and the ECG sensor configured to process the EEG signal and the ECG signal to determine a stress of the user.

In one or more illustrative embodiments, a method for diagnose a user stress in a vehicle, comprises collecting an EEG signal using an EEG sensor installed on a seat, collecting an ECG signal using an ECG sensor installed on the seat, and processing the EEG signal and the ECG signal to determine the user stress using a processor.

In one or more illustrative embodiments, a seat, comprises an EEG sensor installed configured to monitor brain activity of a user and generate a EEG signal; an ECG sensor configured to monitor heart activity of the user and generate a ECG signal; and a processor in communication with the EEG sensor and the ECG sensor configured to process the EEG signal and the ECG signal to determine a stress level of the user.

The details of one or more implementations are set forth in the accompanying drawings and the description below. Other features and advantages will become apparent from the description, the drawings, and the claims.

BRIEF DESCRIPTION OF THE DRAWINGS

For a better understanding of the invention and to show how it may be performed, embodiments thereof will now be described, by way of non-limiting example only, with reference to the accompanying drawings, in which.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The disclosure generally provides for a plurality of circuits or other electrical devices. All references to the circuits and other electrical devices and the functionality provided by each, are not intended to be limited to encompassing only what is illustrated and described herein. While particular labels may be assigned to the various circuits or other electrical devices. Such circuits and other electrical devices may be combined with each other and/or separated in any manner based on the particular type of electrical implementation that is desired. It is recognized that any circuit or other electrical device disclosed herein may include any number of microprocessors, integrated circuits, memory devices (e.g., FLASH, random access memory (RAM), read only memory (ROM), electrically programmable read only memory (EPROM), electrically erasable programmable read only memory (EEPROM), or other suitable variants thereof) and software which co-act with one another to perform operation(s) disclosed herein. In addition, any one or more of the electric devices may be configured to execute a computer-program that is embodied in a non-transitory computer readable medium that is programmed to perform any number of the functions as disclosed.

Arousal may refer to a state or physical and/or psychological activity. In general, stress may occur when a person is having a high degree of arousal accompanied by an unpleasant experience. Heart rate (HR), heart rate variability (HRV), ECG data, and data reflecting brain activities (such as EEG data) may be utilized to identify and diagnose stress. To accurately determine stress, a vehicle integration scheme for ECG waveform identification and diagnostics may be utilized along with an artificial intelligence neuro-fuzzy network. More specifically, the present disclosure proposes a system and methods for determining ECG HR, HRV, and morphological diagnostics of a vehicle user or occupant.

Figure 1:
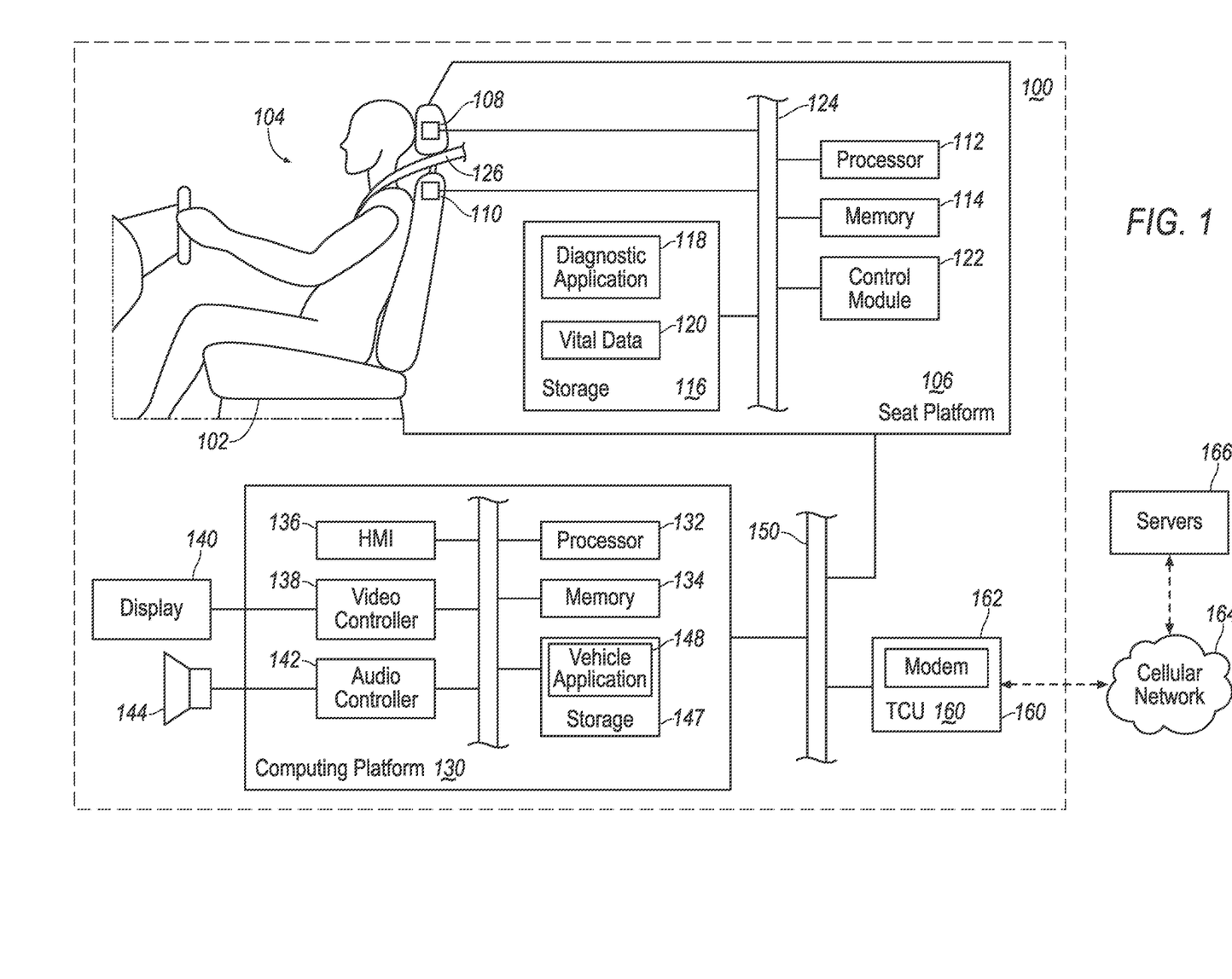
FIG. 1 illustrates an example block topology of a vehicle system of one embodiment of the present disclosure.

FIG. 1 illustrates an example diagram of a system 100 that may be used for the vehicle integration scheme. The vehicle (not shown) may include various types of automobile, crossover utility vehicle (CUV), sport utility vehicle (SUV), truck, recreational vehicle (RV), boat, plane, or other mobile machine for transporting people or goods. In many cases, the vehicle may be powered by an internal combustion engine. As another possibility, the vehicle may be a hybrid electric vehicle (HEV) powered by both an internal combustion engine and one or move electric motors, such as a series hybrid electric vehicle (SHEV), a parallel hybrid electric vehicle (PHEV), or a parallel/series hybrid vehicle (PSHEV), a boat, a plane or other mobile machine for transporting people or goods.

The vehicle may include one or more seats. As illustrated in FIG. 1, a seat platform 106 may include a ECG sensor 110 configured to monitor heartbeats and generate an ECG signal. The ECG sensor 110 may be a capacitive-based sensor as an example. The ECG sensor 110 may also include an integrated breathing sensor (not shown) configured to monitor breathing of the user 104 and generate a breathing signal.

In an example, the ECG sensor 110 may be embedded in a seat cushion at an approximate height level of a user/occupant's 104 chest. In another example, the ECG sensor 110 may be embedded in the seatbelt 126 at an approximate height of the user's 104 chest.

The seat platform 106 may further include an EEG sensor 108 configured to monitor brain activity of the user 104 and generate an EEG signal. The EEG sensor 108 may be a capacitive-based sensor as an example. The seat platform 106 may include a control module 122 configured to control the operation of the seat platform 106. For instance, the control module 122 may be configured to communicate with the ECG sensor 110, the EEG sensor 108 and other components of the seat platform 106 via a seat network 124 to perform various functions. These functions may include storing the ECG signal and EEG signal in a non-volatile manner into a computer-readable storage medium 116 (also referred to as a processor-readable medium or storage) as a vital data 120. The storage 116 includes any non-transitory medium (e.g., tangible medium) that participates in providing instructions or data storage capability for the seat platform 106. In some examples, the seat network 124 may be a separate network from other components of the vehicle. In other examples, the seat network 124 may be a subnet of one or more in-vehicle network 150 which connect various parts of the vehicle together. The in-vehicle network 150 may include, but is not limited to, one or more of a controller area network (CAN), an Ethernet network, and a media oriented system transport (MOST), as some examples.

The seat platform 106 may include one or more processors 112 configured to perform instructions, commands, and other routines in support of the processes described herein. For instance, the seat platform 106 may be configured to execute instructions of diagnostics application 118 to provide detection and diagnostics functions. Such instructions and other data may be maintained in the storage 116. Computer-executable instructions may be compiled or interpreted from computer programs created using a variety of programming languages and/or technologies, including, without limitation, and either alone or in combination, Java, C, C++, C#, Objective C, Fortran, Pascal, Java Script, Python, Perl, and PL/SQL. As an example, the seat platform 106 may be physically installed inside the vehicle seat 102. Alternatively, various components of the seat platform 106 (e.g., the processor 112, memory 114 and storage 116) may be located at elsewhere outside the vehicle seat 102.

The seat platform 106 may be configured to communicate with a computing platform 130 via one or more in-vehicle network 150. The computing platform 130 may include one or more processors 132 configured to perform instructions, commands, and other routines in support of the processes described herein. For instance, the seat platform 106 may be configured to execute instructions of vehicle application 148 to provide features such as navigation, satellite radio decoding, and hands-free calling. Such instructions and other data may be maintained in a non-volatile storage medium 146 (similar to the storage 116 of the seat platform 106). Additionally, the vehicle application 148 may also direct the computing platform 130 to perform detection and diagnostics functions in addition to and/or in place of the seat platform 106.

The computing platform 130 may be provided with various features allowing the vehicle occupants/users to interface with the computing platform 130. For example, the computing platform 130 may receive input from human-machine interface (HMI) controls 136 configured to provide for occupant interaction with the vehicle. As an example, the computing platform 130 may interface with one or more buttons (not shown) or other HMI controls configured to invoke functions on the computing platform 130 (e.g., steering wheel audio buttons, a push-to-talk button, instrument panel controls, etc.). The computing platform 130 may also drive or otherwise communicate with one or more displays 140 configured to provide visual output to vehicle occupants by way of a video controller 138. In some cases, the display 140 may be a touch screen further configured to receive user touch input via the video controller 138, while in other cases the display 140 may be a display only, without touch input capabilities. The computing platform 130 may also drive or otherwise communicate with an audio speaker 144 configured to provide audio output to vehicle occupants by way of an audio controller 142.

The seat platform 106 and the computing platform 130 may further be configured to communicate with a telematics control unit (TCU) 160 via the in-vehicle network 150. The TCU 160 may include one or more wireless modem 162 configured to connect the TCU 160 to a remote server 166 via a cellular network 164 to provide network connectivity.

The seat platform 106 may be configured to perform analysis of the EEG signal from the EEG sensor 108 and the ECG data from the ECG sensor 110. For instance, the seat platform 106 may analyze the EEG signal and perform ECG PQRST waveform identification to diagnose a stress condition of to the user 104 using an artificial intelligence neuro-fuzzy network processing. The seat platform 106 may also diagnose other conditions, including, but not limited to, disturbances of heart rhythm, defects of conduction, ischemic events, and ventricular and atrial enlargements whether primary or as a result of a secondary condition. The seat platform 106 may further provide countermeasures responsive to detection of a stress condition of the user 104.

The seat platform 106 may be configured to automatically start the diagnostics process by generating an initiation signal responsive to detecting a user 104 has entered the vehicle and sat on the car seat 102. For instance, the seat platform 106 may be configured to determine the presence of the user 104 by detecting a weight applied onto the seat 102 or the fastening of the seatbelt 126. Alternatively, the user 104 may manually initiate the diagnostics process using the HMI controls 136 of the computing platform 130 by an action such as pushing a button (not shown) or uttering a voice command, to generate an initiation signal for the control module 122 of the seat platform 106.

The seat platform 106 may send the initiation signal to a control module 122. Responsive to the initiation signal, the control module 122 may be configured to activate the EEG sensor 108 and the ECG sensor 110 to begin collection of vitals of the user 104 for the processor 112 to analyze. The processor 112 may be configured to launch the diagnostics application 118 from the storage 116. The diagnostics application 118 may then process the EEG signal sent from the EEG sensor 108, the ECG signal sent from the ECG sensor 110, and a breathing signal. Additionally, the seat platform 106 may be configured to store those signals sent from the EEG sensor 108 and the ECG sensor 110 into the storage 116 as the vital data 120, and maintain the signals for at least a predefined analysis period of time.

The processor 112 may be configured to perform a variety of processing based on signals sent from the EEG sensor 108 and the ECG sensor 110. In an example, the processor 112 may be configured to determine the user's 104 cardiorespiratory synchronization (CRS) using the ECG signal and the breathing signal sent from the ECG sensor 110. Additionally or alternatively, the processor 112 may be configured to identify a stress level of the user 104 by further analyzing the EEG signal sent from the EEG sensor 108 using the diagnostics application 118.

If the processor 112 determines that the user 104 of the vehicle is encountering stress while operating the vehicle, the vehicle system 100 may be configured to invoke one or more countermeasures intended to reduce the stress level. These countermeasures may facilitate calming the user 104, as operating a vehicle under stress may not be optimal. In an example, the processor 112 may be configured to send a stress signal to the computing platform 130 via the in-vehicle network 150.

Responsive to the receipt of the stress signal, the processor 132 of the computing platform 130 may be configured to launch a countermeasure. In an example, the countermeasure may include commands or other functionality stored in the storage 146. For instance, the countermeasure may be a part of the vehicle application 148. Alternatively, the countermeasure may be provided by the seat platform 106 to the computing platform 130 via the in-vehicle network 150. Or, the countermeasure may be provided by the remote server 166.

As some specific examples of countermeasures, the countermeasure may include instructions for causing the vehicle to play calming music using the speaker 144, or outputting a message instructing the user 104 to slow down or stop the vehicle. Alternatively, when the stress level persists despite the countermeasure, the vehicle system 100 may be configured to contact a third party (e.g., an operator or a doctor) for assistance. For instance, the computing platform 130 may be configured to send a message to the remote server 166 using the TCU 160 via the cellular network 164. The server 166 may relay the message to the third party to notify the third party of the stress condition of the user 104. The seat platform 106 may also upload a portion of the vital data 120 collected from the sensors to the server so that the doctor may have context for use in understanding the situation of the user 104. Concerning privacy of the user 104, only a portion of the vital data 120 is uploaded to the server (e.g., without identifiers of the user 104 or vehicle) and only authorized personnel, such as the doctor of the user 104, may have access to the uploaded data. In case that authorized personnel requests additional data to better understanding the situation, a request may be sent from the server 166 to the seat platform 106 via the TCU 160. Responsive to the request, the user 104 may select via the HMI controls 136 to allow or deny the seat platform 106 to send more vital data 120.

Additionally or alternatively, the analysis and diagnostics may be performed in the computing platform 130 of the vehicle using the processor 132. The seat platform 106 may be configured to load and send the vital data 120 to the computing platform 130 via the in-vehicle network 150 to perform the processing. As an example, the seat platform 106 may be integrated into the computing platform 130 and the signals generated by the EEG sensor 108 and the ECG sensor 110 may be sent to the computing platform 130 for storing and processing.

Additionally or alternatively, the analysis and diagnostics may be performed in a cloud-based manner. In such an example, the vehicle system 100 may be configured to upload the vital data 120 collected by the sensors to the remote server 166 over the cellular network 164 via the TCU 160. Results may then be downloaded by the TCU 160 from the server 166. Since cloud-based implementations may be more bandwidth intensive to the vehicle, the vehicle system 100 may send only a subset of the vital data 120 to the server 166 for processing. For instance, the seat platform 106 may be configured to load and send a sample of the vital data 120 to the server 166 covering a subset of the time of monitoring of the user 104 (e.g., 30 seconds of data every 10 minutes), or a subset of the data (e.g., a decimation or other compression of the data). Alternatively, the seat platform 106 may be configured to send the ECG signal, breathing signal, and only a subset of the EEG signal to the server.

Figure 2:
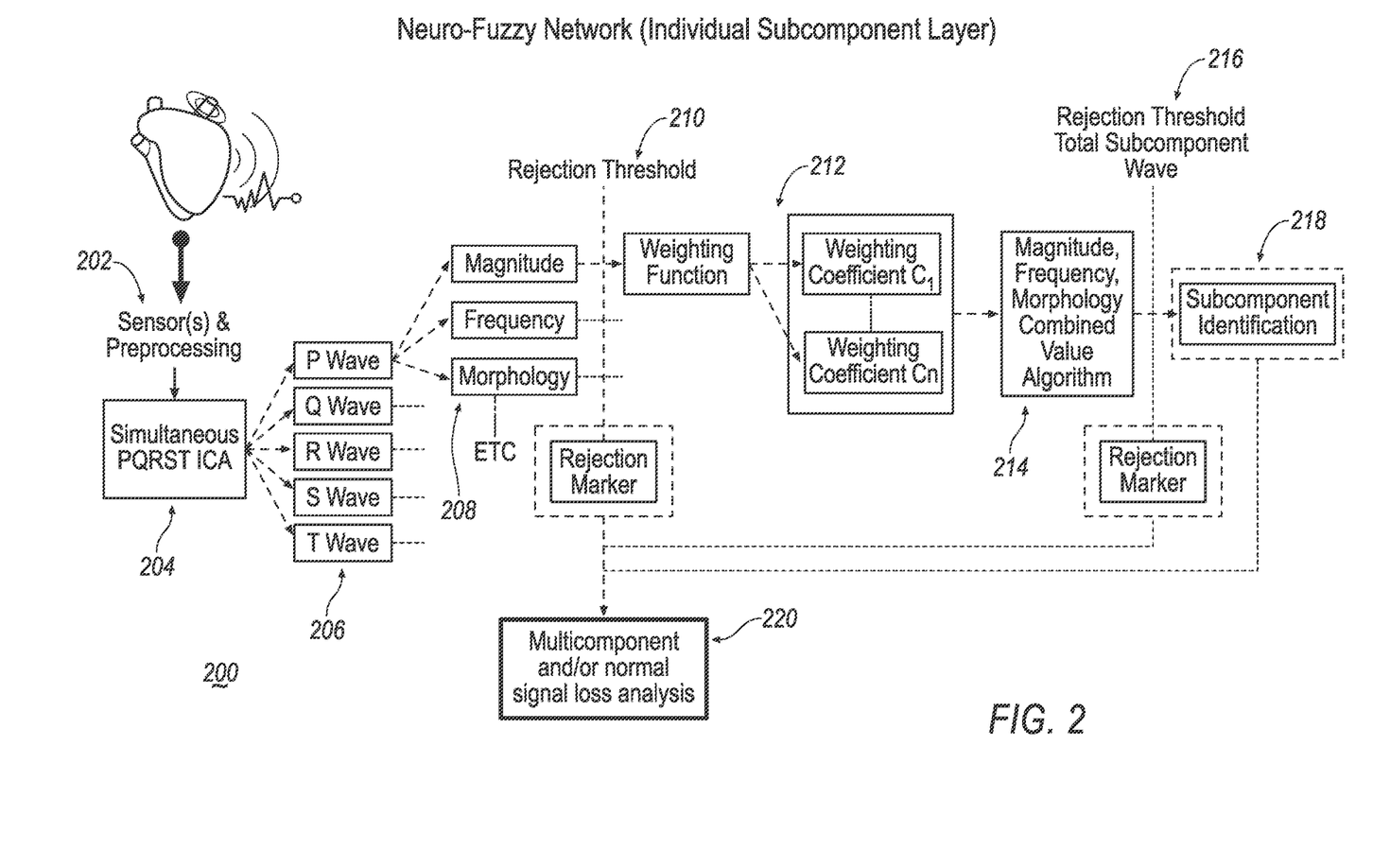
FIG. 2 illustrates an example flow diagram of a process for the neuro-fuzzy network at an individual subcomponent layer.

FIG. 2 illustrates an example flow diagram of a process 200 for the neuro-fuzzy network at the individual subcomponent layer. At 202, the processor 112 of the seat platform 106 may receive the ECG signal sent from the ECG sensor 110 and perform preprocessing of the ECG signal. At 204, the processor 112 may analyzes the ECG signal to extract both linear and nonlinear components of the signal. For instance, advanced methods such as Independent Component Analysis (ICA), Principle component analysis (PCA), and point process theory may be employed to extract important features and information to assess subject status. At 206, the processor 112 divides the ICA signal into a P wave, a Q wave, a R wave, an S wave, and a T wave for individual processing. As shown at 208, the processing of the P wave may include magnitude processing, frequency processing, and morphology processing as some examples. It is noted that although only the processing for the P wave is illustrated in the process 200, operation 206 may include processing for the Q, R, S, T waves as well.

Figure 3:
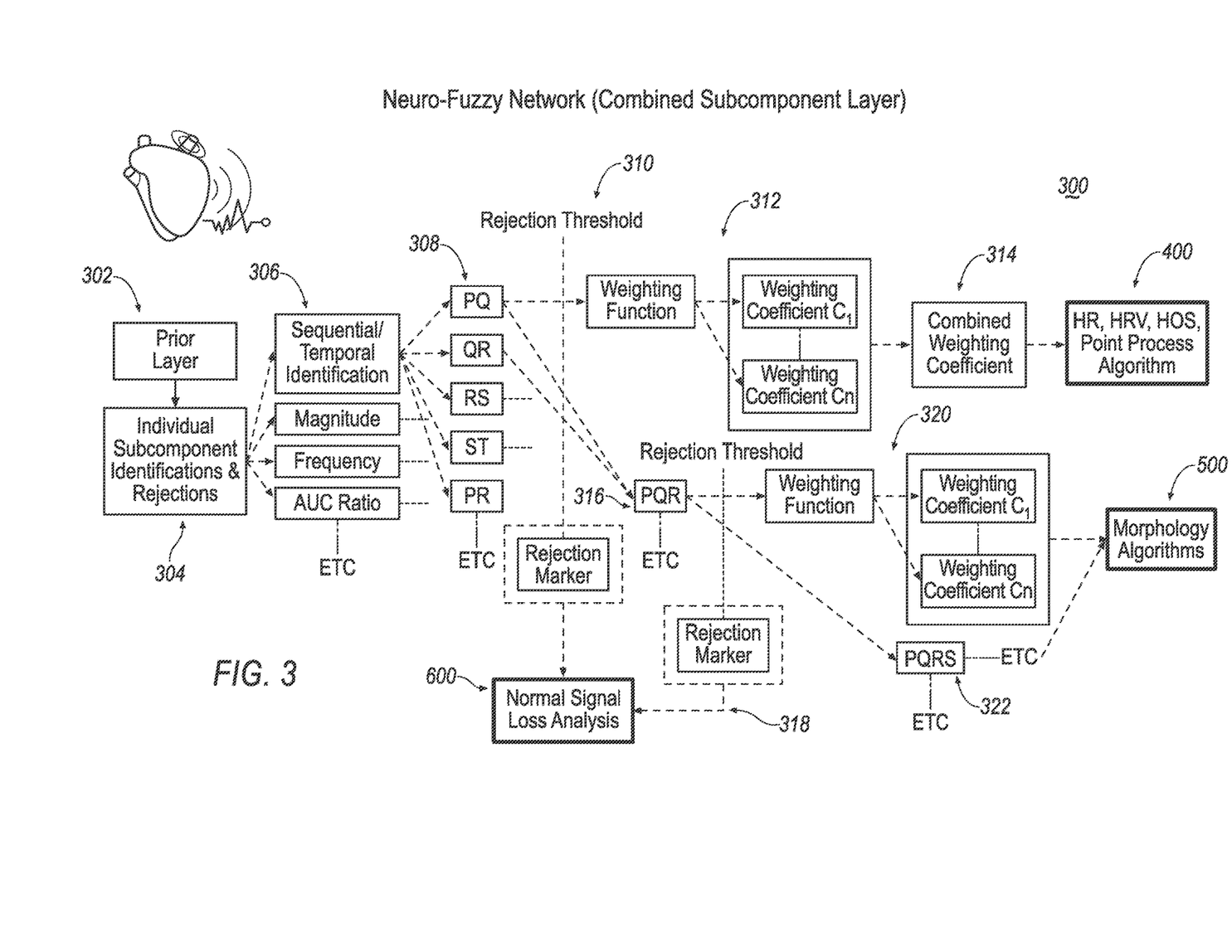
FIG. 3 illustrates an example flow diagram of a process for the neuro-fuzzy network at a combined subcomponent layer.

A rejection threshold may be utilized at 210 to filter out the results of the processing at 208. Signals that passed the rejection test at 210 are further processed by a weighting function at 212. In the weighting function, various weighting coefficient, such as $C_1 \ldots C_N$, may be used. At 214, a magnitude frequency morphology combined value algorithm may be utilized to process the signal. At 216, a second rejection test for the total subcomponent wave may be performed to obtain a subcomponent identification at 218. After operation 218, control then passes to a multi-component and/or normal signal loss analysis 220. Further aspects of this analysis are described with regard to the process 300.

Referring to FIG. 3, an example flow diagram of the process 300 for the neuro-fuzzy network at the combined subcomponent layer is illustrated. The signals processed by the prior layer (e.g., via the process 200) is received at 302. Responsive to receipt of the signals, the processor 112 may perform individual subcomponent identification and rejections on the signals. At 306, signal processing may be performed such as sequential/temporal identification, magnitude processing, frequency processing and area under the curve (AUC) ratio processing. Each signal processing aspect may be performed on combined layers, an example of which is illustrated at 308.

Figure 4:
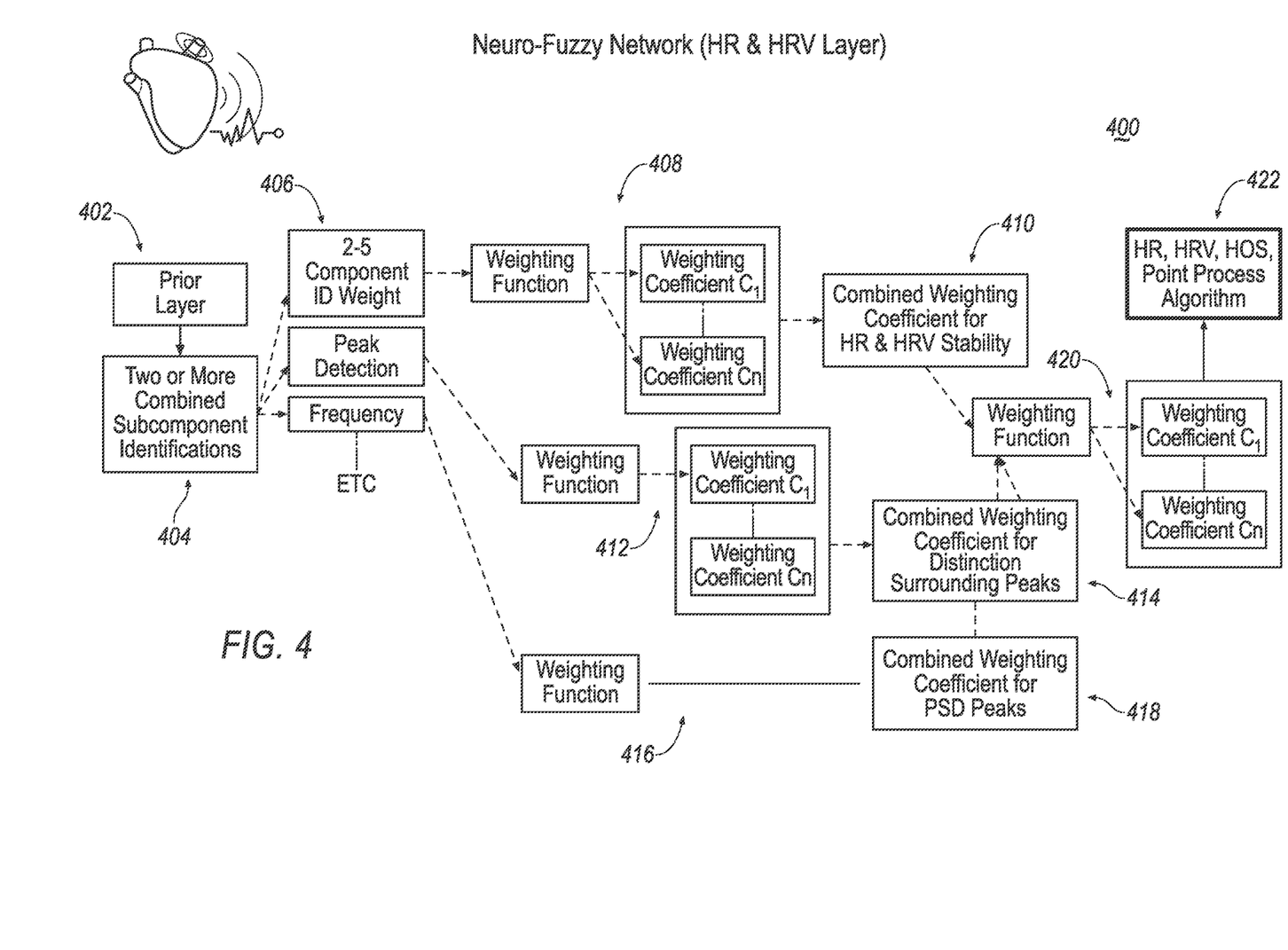
FIG. 4 illustrates an example flow diagram of a process for the neuro-fuzzy network at HR and HRV layers.
Figure 6:
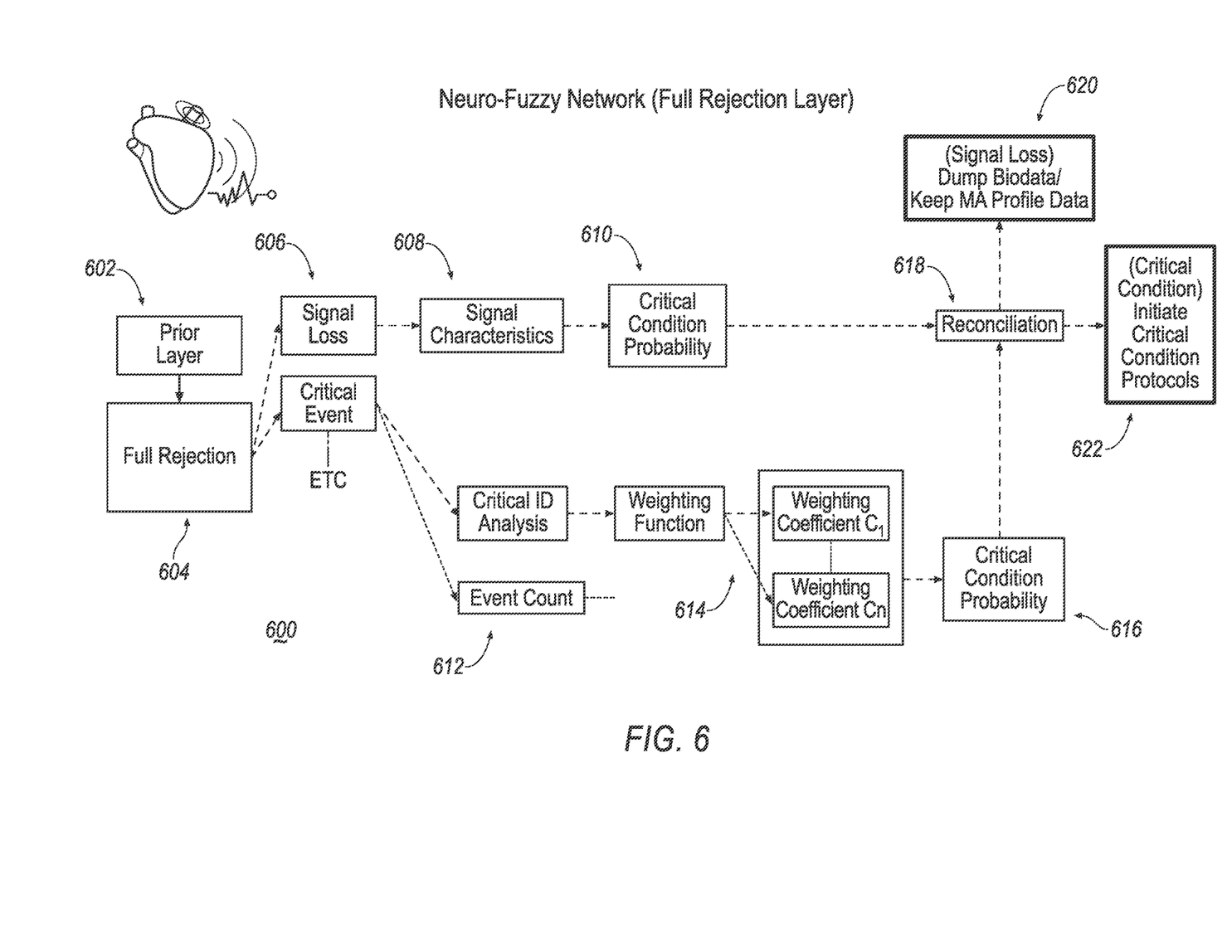
FIG. 6 illustrates an example flow diagram of a process for the neuro-fuzzy network at a full rejection layer.

A rejection threshold may be utilized at 310 to filter out the results of the processing at 308. A rejection marker is utilized for signals that fail to pass the threshold. If the signals fail to pass, control passes to normal signal loss analysis, discussed in detail below with respect to the process 600. Signals that passed the rejection test at 310 are further processed by a weighting function at 312 and various weighting coefficient, such as $C_1 \ldots C_N$, may be used. At 314, the signals are further processed using combined weighting coefficient and the control passes to HR, HRV, Higher Order Spectra (HOS), or a Point Processing algorithm 400.

Figure 5:
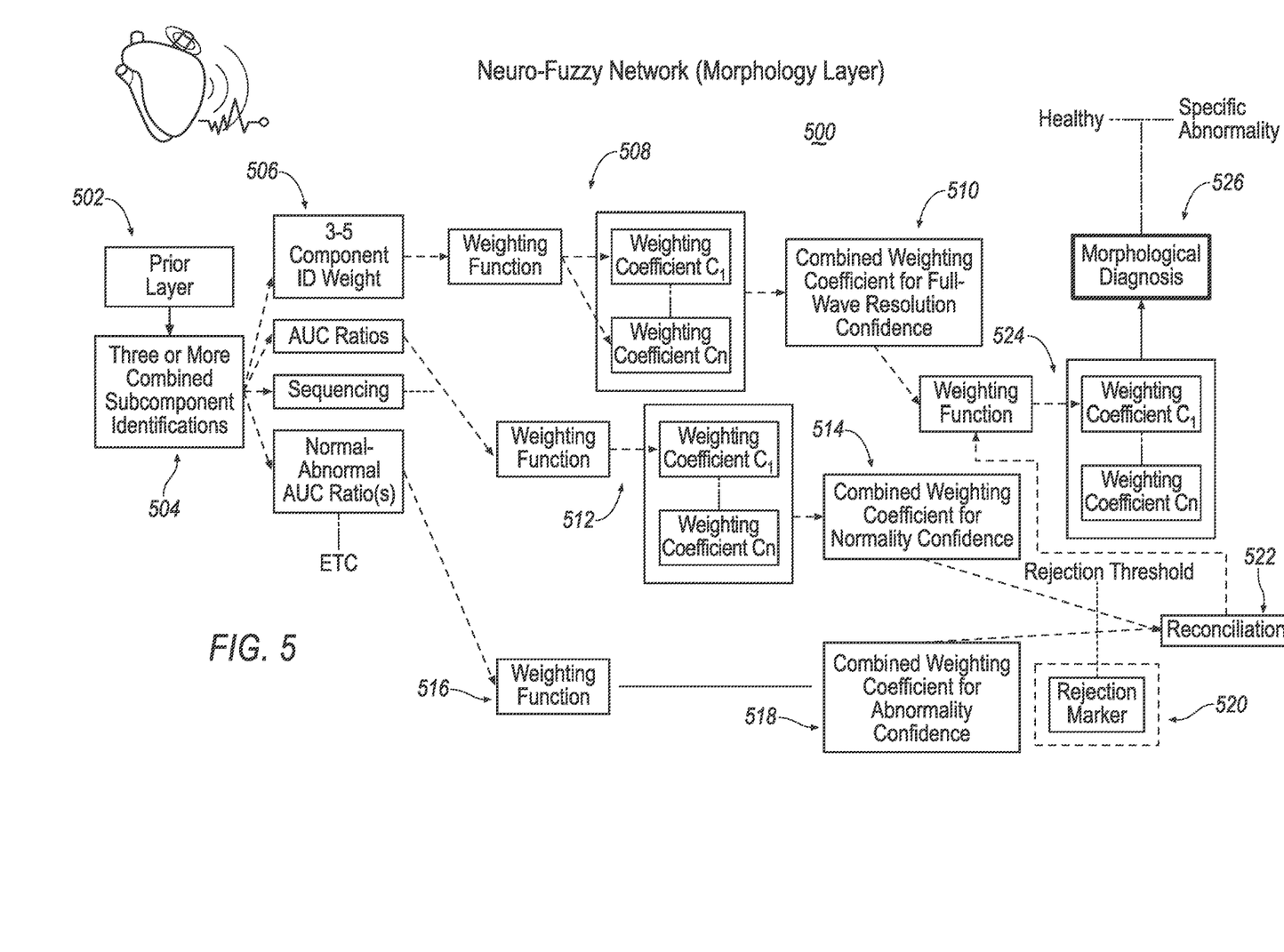
FIG. 5 illustrates an example flow diagram of a process for the neuro-fuzzy network at a morphology layer.

On another branch of the process 300, multiple subcomponents may be further combined at 316. A second rejection threshold may be applied to the further combined subcomponents at 312. If the signal further combined subcomponents do not pass the rejection threshold, the process 300 continues to normal signal loss analysis process 600. Otherwise, if the further combined subcomponents pass the second rejection threshold, a second weighting function having various weighting coefficient, such as $C_1 \ldots C_N$, may be applied. In addition, the subcomponents may be further combined at 322 for a morphology algorithms process 500.

Referring to FIG. 4, an example flow diagram of a process 400 for the neuro-fuzzy network at the HR and HRV layer is illustrated. The signals processed by a prior layer (e.g., via the process 300) is receive at 402, and the processor 112 may perform two or more combined subcomponent identifications at 404. At 406, signal processing such as 2-5 component ID weight, peak detection, and frequency processing may be performed by the processor 112. Following the 2-5 component ID weight 406, a first weighting function having various weighting coefficient, such as $C_1 \ldots C_N$, may be performed at 408. At 410, a combined weighting coefficient for HR & HRV stability is obtained.

Following the peak detection at 406, a second weighting function having various weighting coefficient, such as $C_1 \ldots C_N$, may be performed at 412. At 414, a combined weighting coefficient for distinction of surrounding peaks is obtained. Following the frequency processing at 406, a third weighting function having various weighting coefficient, such as $C_1 \ldots C_N$, may be performed at 416. At 418, a combined weighting coefficient for PSD peaks is obtained.

Taking into account the combined weighting coefficient for HR & HRV stability from 410, the combined weighting coefficient for distinction of surrounding peaks from 414, and the combined weighting coefficient for PSD peaks from 418, a fourth weighting function having various weighting coefficient, such as $C_1 \ldots C_N$, may be performed at 420. At 422 the processor 112 may perform processing using HR, HRV, HOS, or Point Processing algorithms.

Referring to FIG. 5, an example flow diagram of a process 500 for the neuro-fuzzy network at the morphology layer is illustrated. The signals processed by a prior layer is receive at 502 and the processor 112 may perform three or more combined subcomponent identifications at 504. At 506, signal processing such as 3-5 component ID weight, AUC ratio processing, Sequencing processing, and normal-abnormal ACU ratio processing may be performed by the processor 112. Following the 3-5 component ID weight at 506, a first weighting function having various weighting coefficient, such as $C_1 \ldots C_N$, may be performed at 508. At 510, a combined weighting coefficient for full-wave resolution confidence is obtained.

Following the AUC ratio and sequencing processing at 506, a second weighting function having various weighting coefficient, such as $C_1 \ldots C_N$, may be performed at 512. At 514, a combined weighting coefficient for normality confidence is obtained. Following the normal-abnormal AUC ratio processing at 506, a third weighting function having various weighting coefficient, such as $C_1 \ldots C_N$, may be performed at 516. At 518, a combined weighting coefficient for abnormality confidence is obtained.

At 520, a rejection test using a rejection threshold is performed on the combined weighting coefficient for normality confidence from 514 and the combined weighting coefficient for abnormality confidence from 518 to obtain a reconciliation at 522. With the combined weighting coefficient for full-wave resolution confidence from 510 and the reconciliation from 522, a fourth weighting function having various weighting coefficient, such as $C_1 \ldots C_N$, may be performed at 524 to obtain the morphological diagnosis 526 indicative of being health or a specific abnormality.

Referring to FIG. 6, an example flow diagram of a process 600 for the neuro-fuzzy network at a full rejection layer is illustrated. The signals processed by a prior layer is receive at 602 and the processor 112 may perform full rejection at 604. At 606, signal processing such as signal loss and critical event may be performed by the processor 112. Following the signal loss processing, signal characteristics may be analyzed at 608 to determine a critical condition probability at 610. Following the critical event processing, a critical identifier (ID) analysis, and event count may be performed at 612. A weighting function having various weighting coefficient, such as $C_1 \ldots C_N$, may be performed on the result of the critical ID analysis at 614, to determine a critical condition probability at 616. At 618, a reconciliation may be performed on the critical condition probability from 610 and the critical condition probability from 616. As a result, the processor 112 may dump the biodata or keep the MA profile data for signal loss at 620, or initiate critical condition protocols at 622.

Figure 7:
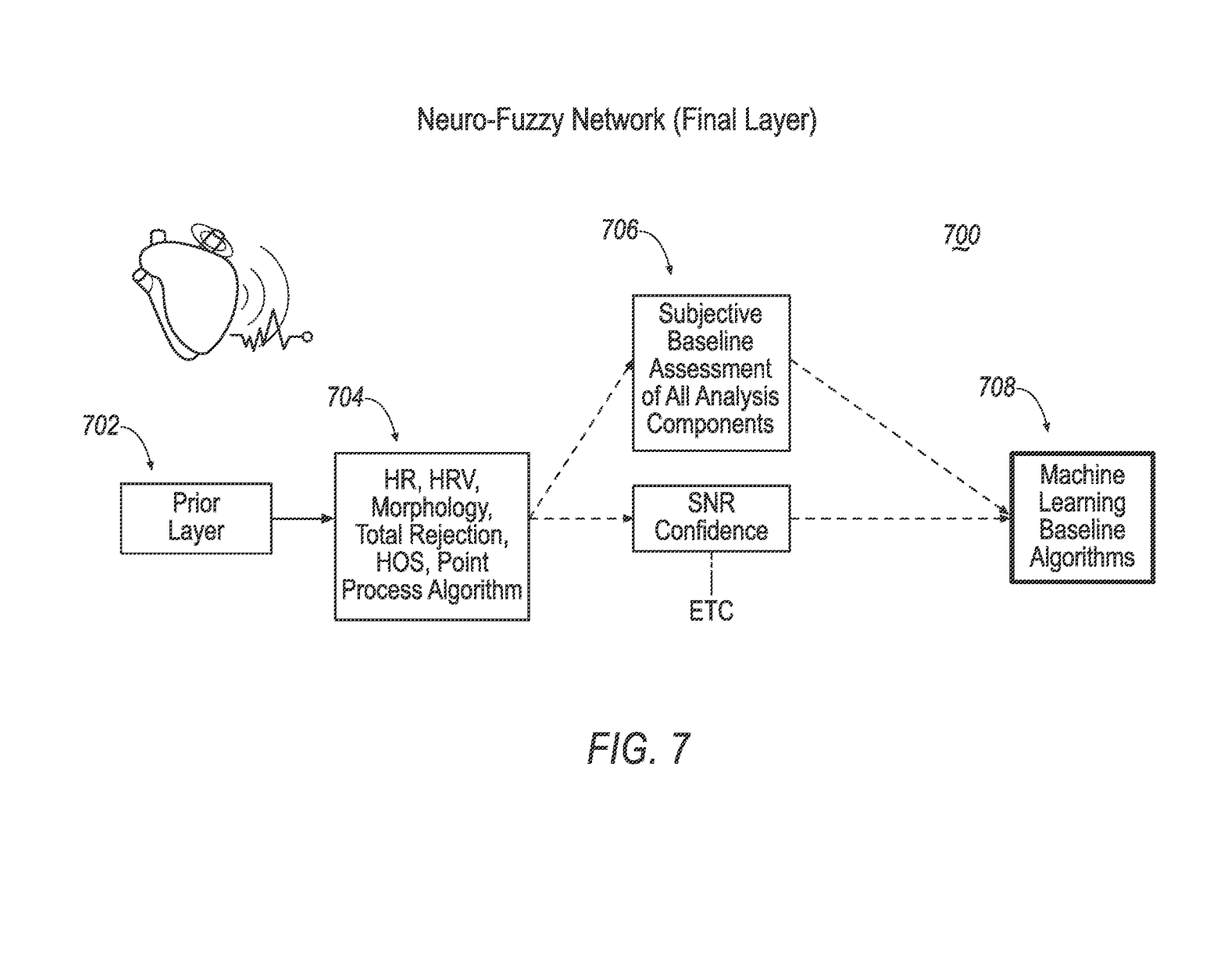
FIG. 7 illustrates an example flow diagram of a process for the neuro-fuzzy network at a final layer.

Referring to FIG. 7, an example flow diagram of a process 700 for the neuro-fuzzy network at a final layer is illustrated. The signals processed by a prior layer is receive at 702 and the processor 112 may perform processing using HR, HRV, morphology, total rejection, HOS, or Point Processing algorithm at 704. At 706, processing such as subjective baseline assessment of all analysis components, and signal-to-noise ratio (SNR) confidence may be performed. At 708 the diagnostics application 118 improves its artificial intelligence through machine learning baseline algorithms.

Figure 8:
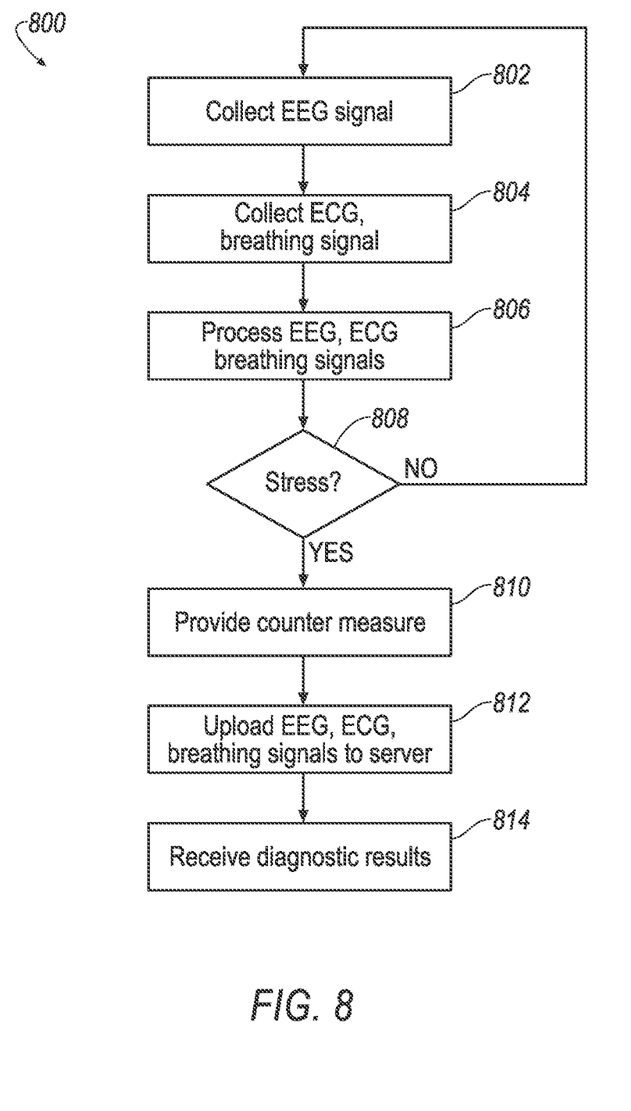
FIG. 8 illustrates an example flow diagram of a process for stress diagnosis of one embodiment of the present disclosure.

Referring to FIG. 8, an example flow diagram of a process 800 for stress diagnosis is illustrated. At operation 802, the seat platform 106 may collect the EEG signal using the EEG sensor 108. At operations 804, the seat platform 106 may collect the ECG and breathing signals using the ECG sensor 110 and the breathing sensor. As discussed previously, the breathing sensor may be integrated with the ECG sensor 110. Alternatively, the breathing sensor may be a separate unit.

At operation 806, the processor 112 of the seat platform 106 may process the EEG, ECG and breathing signals to determine whether the user 104 is experiencing stress. The signals may be processed using the neuro-fuzzy network discussed above referring to FIGS. 2-7. Additionally or alternatively, other signal processing methods or algorithms may also be used to analyze the EEG and ECG signals. For instance, cardiorespiratory synchronization (CRS) may be determined using the ECG and breathing signals. As an alternative example, operation 806 may also be performed at the computing platform 130 using the processor 132. In this case, the EEG, ECG and breathing signals are transmitted from the seat platform 106 to the computing platform 130 via the in-vehicle network 150 responsive to their collection.

At operation 808, if no stress is detected, the control is returned to operation 802 and the seat platform 106 continues to monitor the signals. If stress is detected, the control is passed to operation 810, and the vehicle system 100 may be configured to provide countermeasures responsive to the detection to reduce the stress. As a few nonlimiting examples, the countermeasures may include playing a calming music using the speaker 144, and outputting a message instructing the user 104 to slow down or stop the vehicle.

In addition to providing the countermeasures, at operation 812, the vehicle system 100 may be further configured to upload the EEG, ECG and breathing signals to the server 166 using the TCU 160 via the cellular network 164 for further analysis. Alternatively, the computing platform 130 may be configured to only send a message indicative of the detection of stress to the server 166 instead of uploading the vital signals. The server 166 may be configured to further process the vital signals sent from the computing system 100 to further diagnose the stress condition of the occupant 104. In addition, the server 166 may be configured to send the diagnostic results back to the vehicle system 100. Alternatively, the results may be sent to a third party, such as a doctor, for assistance.

At operation 814, the vehicle system 100 may receive diagnostic results from the server 166. As an example, the diagnostic results may be stored in the storage 116 of the seat platform 106 or the storage 146 of the computing platform 130 for further use.

Computing devices described herein, generally include computer-executable instructions where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, C#, Visual Basic, JavaScript, Python, JavaScript, Perl, PL/SQL, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined not with reference to the above description, but with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The abstract of the disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A vehicle system, comprising:
an electroencephalography (EEG) sensor, installed on a seat and configured to monitor brain activity of a user located in the seat to generate a EEG signal;
an electrocardiogram (ECG) sensor, installed on the seat and configured to monitor heart activity of the user to generate an ECG signal;
a processor, in communication with the EEG sensor and the ECG sensor, configured to process vital data, the vital data including the EEG signal and the ECG signal, to determine a stress level of the user;
responsive to the stress level being above a predefined threshold, output a countermeasure to the user;
responsive to the stress level persisting for a predefined period of time, upload a first portion of the vital data indicative of the stress to a server for analysis in an anonymous manner;
responsive to receiving a request for additional vital data from the server, output a message via a human-machine interface (HMI) to request user permission to grant access to additional vital data; and
responsive to receiving the user permission via the HMI, upload a second portion of the vital data corresponding to the stress to the server in a non-anonymous manner.

2. The vehicle system of claim 1, wherein the countermeasure includes at least one of to: play a previously-recorded audio file intended to elicit a calming effect, invite the user to slow down or stop the vehicle, or send a message to a third party.

3. The vehicle system of claim 1, further comprising a breathing sensor, installed on the seat and configured to monitor breathing activity of the user to generate a breathing signal.

4. The vehicle system of claim 3, wherein the breathing sensor is combined with the ECG sensor as a single unit.

5. The vehicle system of claim 3, wherein the processor is further configured to analyze a cardiorespiratory synchronization using the ECG signal and the breathing signal.

6. The vehicle system of claim 1, wherein the processor is further configured to communicate with a telematics controller to upload one or more of the EEG signal and the ECG signal to a server.

7. The vehicle system of claim 6, wherein the telematics controller is further configured to receive a diagnostic result from a server.

8. The vehicle system of claim 6, wherein the telematics controller is further configured to receive instruction to perform the countermeasure from the server, and the processor is configured to execute the countermeasure responsive to receipt of the instruction.

9. The vehicle system of claim 6, wherein the processor is further configured to communicate with an infotainment system, the telematics controller is further configured to receive a request from the server for additional EEG and ECG signals, and the infotainment system is configured to prompt the user to accept or deny the request.

10. The vehicle system of claim 1, further comprising a storage, installed to the seat and configured to record the EEG signal and the ECG signal.

11. A method for diagnosing user stress in a vehicle, comprising:
    collecting an electroencephalography (EEG) signal using an EEG sensor installed on a vehicle seat;
    collecting an electrocardiogram (ECG) signal using an ECG sensor installed on the vehicle seat;
    processing vital data, the vital data including the EEG signal and the ECG signal, to determine a level of stress of the user;
    continuously uploading, via a telematics controller, the ECG signal to a server for diagnosis;
    periodically uploading, via the telematics controller, a subset of the EEG signal to the server for diagnosis; and
    responsive to receiving a diagnosis result indicative of a level of stress above a predefined threshold, output a countermeasure to the user.

12. The method of claim 11, wherein the countermeasure includes at least one of: playing a previously-recorded audio file intended to elicit a calming effect, inviting the user to slow down or stop the vehicle, or sending a message to a third party.

13. The method of claim 11, further comprising:
    receiving, using the telematics controller, instruction to perform the countermeasure from the server; and
    executing the countermeasure responsive to receipt of the instruction.

14. A seat, comprising:
    an electroencephalography (EEG) sensor configured to monitor brain activity of a user sitting on the seat and generate a EEG signal;
    an electrocardiogram (ECG) sensor configured to monitor heart activity of the user and generate a ECG signal; and
    a processor in communication with the EEG sensor and the ECG sensor configured to
        process vital data, the vital data including the EEG signal and the ECG signal, to determine a stress level of the user
        continuously upload the ECG signal to a server for diagnosis;
        periodically upload a subset of the EEG signal to the server for diagnosis; and
        responsive to receive a diagnosis result indicative of a level of stress above a predefined threshold, output a countermeasure to the user.

15. The seat of claim 14, wherein the processor is further configured to:
    responsive to the stress level persisting for a predefined period of time, upload a first portion of the vital data to a server for analysis in an anonymous manner;
    responsive to receiving a request for additional vital data from the server, output a message via a human-machine interface (HMI) to request a user permission to grant access to additional vital data; and
    responsive to receiving the user permission via the HMI, upload a second portion of vital data to the server.

16. The method of claim 11, further comprising:
    responsive to the stress level persisting for a predefined period of time despite the countermeasure, uploading a first portion of the vital data indicative of the stress to a server for analysis in an anonymous manner;
    responsive to receiving a request for additional vital data from the server, outputting a message via a human-machine interface (HMI) to request a user permission to grant access to more vital data; and
    responsive to receiving the user permission via the HMI, uploading a second portion of vital data indicative of the stress to the server.

* * * * *